US00RE42857E

(19) United States
(12) Reissued Patent
Cali et al.

(10) Patent Number: US RE42,857 E
(45) Date of Reissued Patent: Oct. 18, 2011

(54) METHOD OF LASER CUTTING PERICARDIAL TISSUE FOR USE WITH AN IMPLANTABLE MEDICAL DEVICE

(75) Inventors: Douglas S. Cali, Mission Viejo, CA (US); Keith E. Myers, Lake Forest, CA (US)

(73) Assignee: 3F Therapeutics, Inc., Lake Forest, CA (US)

(21) Appl. No.: 12/765,356

(22) Filed: Apr. 22, 2010

Related U.S. Patent Documents

Reissue of:

(64) Patent No.: 6,872,226
Issued: Mar. 29, 2005
Appl. No.: 10/207,438
PCT Filed: Jul. 26, 2002

U.S. Applications:

(63) Continuation-in-part of application No. 09/772,526, filed on Jan. 29, 2001, now Pat. No. 6,682,559.

(60) Provisional application No. 60/308,268, filed on Jul. 26, 2001, provisional application No. 60/178,333, filed on Jan. 27, 2000.

(51) Int. Cl.
*A61F 2/24* (2006.01)

(52) U.S. Cl. ..... 623/2.13; 600/36

(58) Field of Classification Search ..... 600/36; 94/94.11; 623/1.44, 2.13, 901, 915–918; 372/25

See application file for complete search history.

(56) References Cited

U.S. PATENT DOCUMENTS

| | | | |
|---|---|---|---|
| 3,608,097 | A | 9/1971 | Bellhouse et al. |
| 3,671,979 | A | 6/1972 | Moulopoulos |
| 4,056,854 | A | 11/1977 | Boretos et al. |
| 4,106,129 | A | 8/1978 | Carpentier et al. |
| 4,222,126 | A | 9/1980 | Boretos et al. |
| 4,261,342 | A | 4/1981 | Aranguren Duo |
| 4,274,437 | A | 6/1981 | Watts |
| 4,297,749 | A | 11/1981 | Davis et al. |
| 4,388,735 | A | 6/1983 | Ionescu et al. |
| 4,470,157 | A | 9/1984 | Love |
| 4,501,030 | A | 2/1985 | Lane |

(Continued)

FOREIGN PATENT DOCUMENTS

EP 0051451 5/1982

(Continued)

OTHER PUBLICATIONS

Roe, Benson B., "'Extinct' Cardiac Valve Prostheses", Replacement Cardiac Valves, 1991, pp. 307-332, Pergamon Press, Inc., New York.

(Continued)

*Primary Examiner* — Brian E. Pellegrino

(57) ABSTRACT

A method of cutting material for use in an implantable medical device employs a plotted laser cutting system. The laser cutting system is computer controlled and includes a laser combined with a motion system. The laser precisely cuts segments out of source material according to a predetermined pattern as designated by the computer. The segments are used in constructing implantable medical devices. The cutting energy of the laser is selected so that the cut edges of the segments are melted to discourage delamination or fraying, but communication of thermal energy into the segment beyond the edge is minimized to avoid damaging the segment adjacent the edge.

9 Claims, 7 Drawing Sheets

U.S. PATENT DOCUMENTS

| | | | | |
|---|---|---|---|---|
| 4,624,822 | A | | 11/1986 | Arru et al. |
| 4,626,255 | A | | 12/1986 | Reichart et al. |
| 4,629,459 | A | | 12/1986 | Ionescu et al. |
| 4,739,487 | A | | 4/1988 | Bonnet et al. |
| 4,787,901 | A | | 11/1988 | Baykut |
| 4,790,844 | A | | 12/1988 | Ovil |
| 4,960,424 | A | | 10/1990 | Grooters |
| 5,032,128 | A | | 7/1991 | Alonso |
| 5,037,434 | A | | 8/1991 | Lane |
| 5,089,971 | A | | 2/1992 | Gerber |
| 5,163,955 | A | | 11/1992 | Love et al. |
| 5,258,917 | A | | 11/1993 | Bruder et al. |
| 5,326,370 | A | | 7/1994 | Love et al. |
| 5,332,402 | A | | 7/1994 | Teitelbaum |
| 5,344,442 | A | | 9/1994 | Deac |
| 5,370,685 | A | | 12/1994 | Stevens |
| 5,411,552 | A | | 5/1995 | Andersen et al. |
| 5,415,667 | A | | 5/1995 | Frater |
| 5,422,899 | A | * | 6/1995 | Freiberg et al. ..... 372/25 |
| 5,480,424 | A | | 1/1996 | Cox |
| 5,489,298 | A | | 2/1996 | Love et al. |
| 5,500,015 | A | | 3/1996 | Deac |
| 5,554,184 | A | | 9/1996 | Machiraju |
| 5,713,950 | A | | 2/1998 | Cox |
| 5,713,953 | A | | 2/1998 | Vallana et al. |
| 5,757,950 | A | | 5/1998 | Bruder |
| 5,824,063 | A | | 10/1998 | Cox |
| 5,824,065 | A | | 10/1998 | Gross |
| 5,824,067 | A | | 10/1998 | Gross |
| 5,838,569 | A | | 11/1998 | Gane |
| 5,849,006 | A | | 12/1998 | Frey et al. |
| 5,861,028 | A | | 1/1999 | Angell |
| 5,928,281 | A | | 7/1999 | Huynh et al. |
| 5,961,549 | A | | 10/1999 | Nguyen et al. |
| 6,092,529 | A | | 7/2000 | Cox |
| 6,129,758 | A | | 10/2000 | Love |
| 6,254,636 | B1 | | 7/2001 | Peredo |
| 6,338,740 | B1 | | 1/2002 | Carpentier |
| 6,350,282 | B1 | | 2/2002 | Eberhardt |
| 6,378,221 | B1 | | 4/2002 | Ekholm, Jr. et al. |
| 6,454,799 | B1 | | 9/2002 | Schreck |
| 6,461,382 | B1 | | 10/2002 | Cao |
| 6,463,351 | B1 | | 10/2002 | Clynch |
| 6,475,239 | B1 | | 11/2002 | Campbell et al. |
| 6,553,681 | B2 | | 4/2003 | Ekholm, Jr. et al. |
| 6,652,578 | B2 | | 11/2003 | Bailey et al. |
| 6,801,643 | B2 | | 10/2004 | Pieper |
| 6,911,043 | B2 | | 6/2005 | Myers et al. |
| 7,594,974 | B2 | | 9/2009 | Cali et al. |
| 2001/0021872 | A1 | | 9/2001 | Bailey et al. |
| 2002/0091441 | A1 | | 7/2002 | Guzik |
| 2002/0157271 | A1 | | 10/2002 | Ekholm, Jr. et al. |
| 2002/0191822 | A1 | | 12/2002 | Pieper |

FOREIGN PATENT DOCUMENTS

| | | | | |
|---|---|---|---|---|
| EP | 0103546 | | | 3/1984 |
| EP | 0276975 | | | 8/1988 |
| EP | 0515324 | | | 11/1992 |
| FR | 2591100 | | | 6/1987 |
| GB | 1599407 | | | 9/1981 |
| WO | WO 91/17720 | | | 11/1991 |
| WO | WO 91/19465 | | | 12/1991 |
| WO | WO 92/20303 | | | 11/1992 |
| WO | WO 9724081 | A1 | * | 7/1997 |
| WO | WO 99/30884 | | | 6/1999 |
| WO | WO 00/42950 | | | 7/2000 |
| WO | WO 01/54624 | | | 8/2001 |
| WO | WO 01/54624 | A1 | | 8/2001 |
| WO | WO 01/76510 | | | 10/2001 |
| WO | WO 02/24118 | | | 3/2002 |
| WO | WO 02/053069 | | | 7/2002 |
| WO | WO 02/053069 | A2 | | 7/2002 |

OTHER PUBLICATIONS

Love, Charles S., B.A., et al.,"The Autogenous Tissue Heart Valve: Current Status", Journal of Cardiac Surgery, 1991, pp. 499-507, vol. 6, No. 4, Futurua Publishing Company Inc., New York.

Hubka, et al., "Replacement of Mitral and Tricuspid Valves by Mitral Homograft", The Journal of Thoracic and Cardiovascular Surgery, vol. 51, No. 2, Feb. 1966, pp. 195-204.

Holdefer, et al., "An Experimental Approach to Mitral Valve Replacement with Autologous Pericardium", The Journal of Thoracic and Cardiovascular Surgery, vol. 55, No. 6, Jun. 1968, pp. 873-881.

Suzuki, Akio, M.D., et al., "Mitral Valve Replacement with Transplant Valves", The Journal of Thoracic and Cardiovascular Surgery, vol. 60, No. 1, Jul. 1970, pp. 13-25.

Mickleborogh, et al.,"A Simplified Concept for a Bileaflet Atrioventricular Valve That Maintains Annular-Papillary Muscle Continuity", The Journal of Thoracic and Cardiovascular Surgery, vol. 4, No. 1, Mar. 1989, pp. 58-65.

Athanasuleas, et al., "The Autologous Rectus Sheath Cardiac Valve", The Journal of Thoracic and Cardiovascular Surgery, vol. 65, No. 1, Jan. 1973, pp. 118-123.

Edwards, W. Sterling, et al., "Partial and Complete Reconstruction of the Mitral Valve with Pericardium", Prosthetic Heart Valves, 1969, pp. 820-831.

Van Der Spuy, J.C., "Completely Anatomical Autogenous Whole Mitral Valve", Thorax, 1964, 19, pp. 526-529.

Schimert, George, M.D., et al., "Fabrication of Mitral Leaflets and Aortic Cusps From Silastic Rubbercoated Teflon Felt", Prosthetic Valves for Cardiac Surgery, pp. 368-384.

Endre Bodnar, M.D., et al., *Replacement Cardiac Valves,* Pergamon Press, (New York), 1991, pp. 307-332.

* cited by examiner

FIG. 1
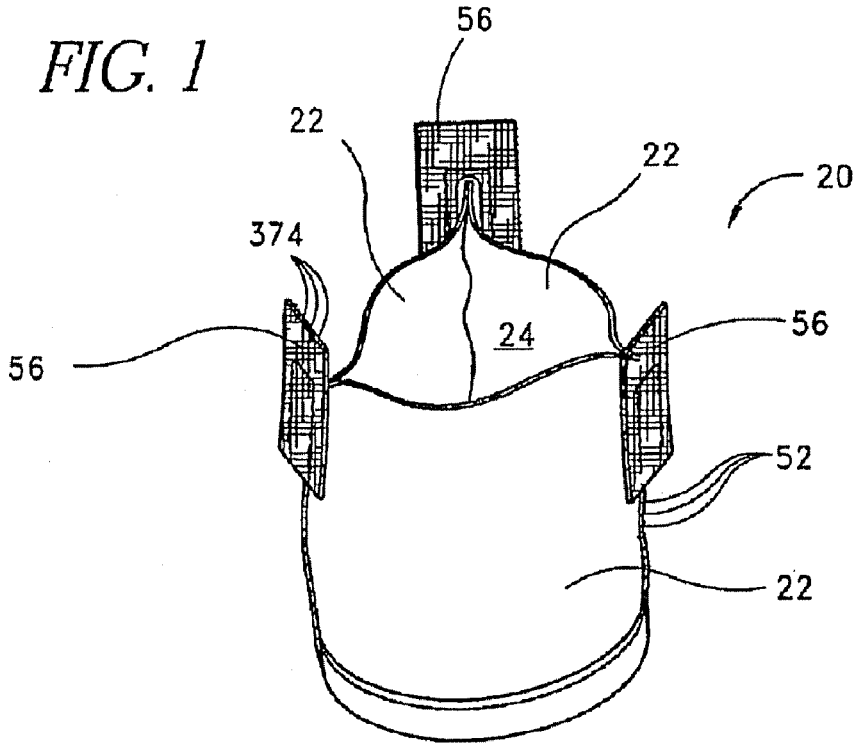
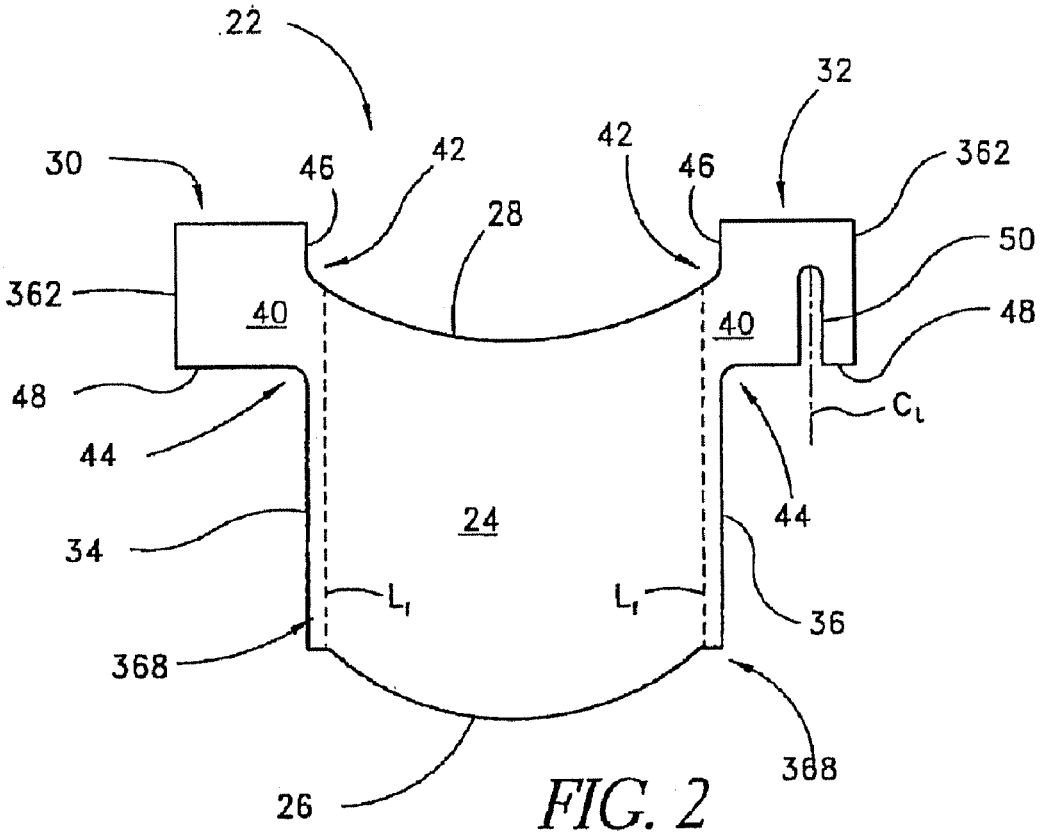
FIG. 2

METHOD OF LASER CUTTING PERICARDIAL TISSUE FOR USE WITH AN IMPLANTABLE MEDICAL DEVICE

Matter enclosed in heavy brackets [ ] appears in the original patent but forms no part of this reissue specification; matter printed in italics indicates the additions made by reissue.

RELATED APPLICATIONS

This application is a continuation-in-part of U.S. application Ser. No. 09/772,526, now U.S. Pat. No. 6,682,559, entitled PROSTHETIC HEART VALVE; which was filed on Jan. 29, 2001 *and which claims the benefit of priority of U.S. Provisional Application No. 60/178,333, which was filed on Jan. 27, 2000*. This application also claims priority to U.S. Provisional Application No. 60/308,268, which was filed on Jul. 26, 2001. [The above priority applications] *Application Ser. Nos. 09/772,526 and 60/308,268* are hereby incorporated by reference in their entirety.

BACKGROUND OF THE INVENTION

1. Field of the Invention

This invention relates to implantable medical devices, and more particularly relates to forming segments used to construct such implantable medical devices.

2. Description of the Related Art

Medical devices are often surgically implanted into a patient in order to assist or replace diseased tissue. For instance, a prosthetic device such as an artificial heart valve can be implanted to replace a defective natural heart valve.

It is important for such prosthetic devices to be substantially durable, as failure of the device may have drastic consequences for the patient. As can be appreciated, a prosthetic device that wears out prematurely may put a patient at substantial risk, both because of the possibility of early, sudden failure of the device and because of additional surgery that may be required to replace the device.

Some implantable medical devices comprise two or more members or segments of material that are assembled to form the device. The manner in which the segments of material are formed can significantly affect the durability of the device. For example, if the segments are formed by being cut out of a larger portion of material, the edges of the cut segments may be especially susceptible to premature wear. Also, imprecise cutting or inconsistencies between cut segments may negatively affect both the operability and durability of the assembled prosthetic device.

SUMMARY OF THE INVENTION

Accordingly, there is a need for a method and apparatus for cutting segments of material for use in implantable medical devices wherein the segments are cut with precision and consistency, and wherein the cut edges of the segments resist wear when implanted into the body.

In accordance with one embodiment, a method of creating an implantable medical prosthesis is provided. A sheet of pericardium having at least two tissue layers is provided and a segment of tissue is cut out of the sheet of pericardium with a laser beam. The cutting comprises operating a laser at a power and pulse rate such that the beam welds the layers of the pericardium together along a laser cut edge without significantly burning the pericardium adjacent the cut edge.

For purposes of summarizing the invention and the advantages achieved over the prior art, certain aspects and advantages of the invention have been described herein above. Of course, it is to be understood that not necessarily all such aspects or advantages may be achieved in accordance with any particular embodiment of the invention. Thus, for example, those skilled in the art will recognize that the invention may be embodied or carried out in a manner that employs one or more aspects to achieve or optimize one advantage or group of advantages as taught herein without necessarily using other aspects or achieving other advantages as may be taught or suggested herein.

All of these aspects are intended to be within the scope of the invention herein disclosed. These and other aspects of the present invention will become readily apparent to those skilled in the art from the following detailed description of the preferred embodiments having reference to the attached figures, the invention not being limited to any particular preferred embodiment(s) disclosed.

BRIEF DESCRIPTION OF THE DRAWINGS

FIG. 1 is a perspective view of a prosthetic aortic heart valve constructed by joining three independently formed leaflets together.

FIG. 2 shows a flat pattern for a leaflet to be used in constructing the heart valve of FIG. 1.

DETAILED DESCRIPTION OF A PREFERRED EMBODIMENT

Figure 3:
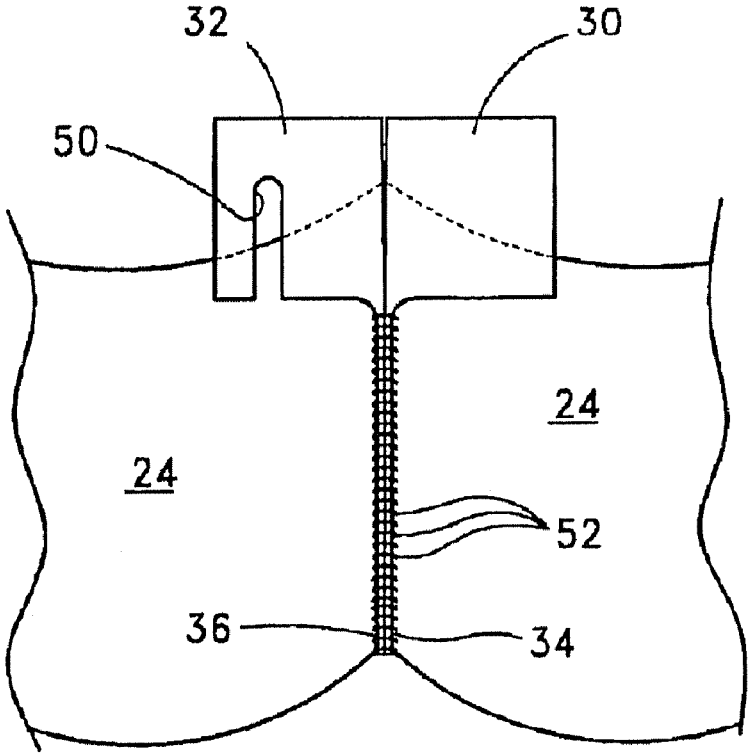
FIG. 3 shows two adjacent leaflets of the valve of FIG. 1 during valve assembly.

The present invention can be used to cut out segments used when constructing several types of prostheses. One type of prosthesis that particularly benefits from use of the present invention is a replacement heart valve having one or more leaflets that are cut from a source material and assembled to form the valve. FIGS. 1-4 present a prosthetic aortic heart valve 20 constructed in accordance with an embodiment of the present invention. This heart valve 20 is discussed in order to help illustrate aspects and advantages of the invention and is discussed in more detail in the above-referenced application entitled PROSTHETIC HEART VALVE. It is to be understood that other types of implantable prostheses may also benefit from the aspects discussed below.

The aortic heart valve 20 of FIGS. 1-4 comprises three leaflets 22 that are cut out of a generally flat, flexible source material. Each of the three leaflets 22 is cut out according to the pattern shown in FIG. 2. As shown, each leaflet 22 has a main body 24 that is scalloped at both its proximal and distal ends 26, 28. First and second distal tab portions 30, 32 extend outwardly from corresponding first and second side edges 34, 36 of each leaflet's main body 24. The tabs 30, 32 are substantially rectangular in shape and extend distally beyond the distal end 28 of the main body 24.

Each of the tabs 30, 32 communicate with the leaflet main body 24 through a neck portion 40. Curved transition edges 42, 44 connect an inner edge 46 of each tab 30, 32 with the distal end 28 of the leaflet 22, and a proximal edge 48 of each tab 30, 32 with the corresponding side edge 34, 36 of the leaflet 22. An elongate slot 50 is formed in the second tab 32. The slot 50 extends distally from the proximal edge 48 of the tab to a point just distal of the distal-most edge 28 of the leaflet main body 24.

With reference next to FIG. 3, adjacent leaflets are connected by aligning the first outer edge 34 of one leaflet with the second outer edge 36 of the adjacent leaflet so that the inner faces of the leaflets engage one another. The side edges 34, 36 are sutured together using a series of locked stitches 52 arranged along a fold line $L_F$ adjacent each side edge 34, 36.

Figure 4:
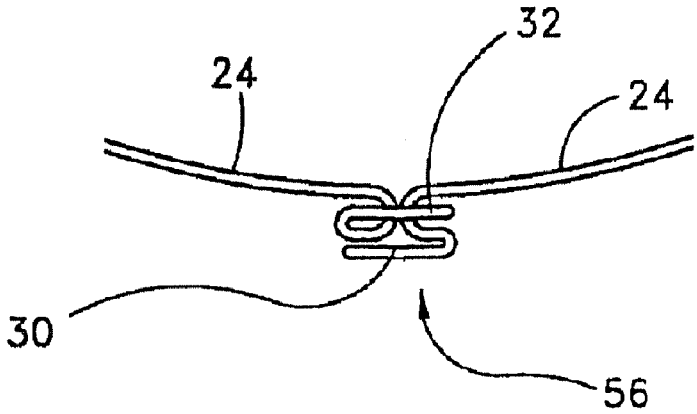
FIG. 4 is a top view showing the leaflets of FIG. 3 folded over each other in a desired manner to form a commissural tab.

The series of sutures 52 terminates prior to reaching the proximal edge 48 of the tabs 30, 32, with the last suture being placed proximal of the proximal transition edge 44. The tabs 30, 32 are then folded backwardly along the fold line $L_F$ so as to overlap the outer surface of their respective leaflets 22, as shown in FIG. 3. With reference next to FIG. 4, the adjacent first and second tabs 30, 32 are folded over one another in order to form commissural tabs 56. More specifically, the second tab 32 is folded so that the slot 50 straddles the neck portions 40 of both tabs 30, 32. The first tab 30 is folded opposite the second tab 32 and generally aligned with the second tab 32, as shown in FIG. 4. The folded tabs 30, 32 are then sewn together in order to form the commissural tabs 56 shown in FIG. 1.

In the illustrated embodiment, each of the leaflets 22 is substantially identical in shape. It is to be understood, however, that other prosthetic devices may employ segments of varying sizes and shapes. For example, a prosthetic mitral heart valve can employ two leaflets which are shaped differently from one another. However to maintain consistency in manufacture, the respective leaflets preferably are substantially identical in size and shape from valve to valve. Additionally, prosthetic devices such as surgical patches may desirably be produced in several sizes and shapes.

Replacement valves such as the aortic valve 20 illustrated in FIGS. 1-4 are used to replace diseased natural valves. The natural valve is cut out of its place and removed, leaving a valve annulus and a plurality of downstream attachment locations. The inflow annulus of the replacement valve is configured to fit into the valve annulus vacated by the native aortic valve. The commissural attachment tabs 56 can be attached to the aorta at points vacated by the native valve's commissural attachment locations. The replacement valve thus totally replaces the native valve.

Once installed, the replacement valve functions much the same as a native aortic valve. During systole, the leaflets 22 are forced apart so that blood flows freely through the valve 20 and into the aorta. During diastole, the leaflets are drawn toward each other and approximate each other, thus sealing the valve. The commissural attachment tabs 56 help prevent the valve leaflets from prolapsing during diastole.

In the illustrated embodiment, the leaflets can be constructed of biological or synthetic materials. For example, explanted human or animal tissue, such as bovine, porcine and kangaroo pericardium tissue may be appropriately used. Synthetic material, such as polyesters, Teflon®, fluoropolymers, woven or knitted cloth, etc. can also be used. Of course, biological and synthetic materials not listed above can be used if appropriate. Leaflet materials for the illustrated heart valve can be selected using a general guideline that the more pliable, thin and strong a material is, the better. Additionally, it is advantageous for the material to be as nonthrombogenic as possible.

In a preferred embodiment, the flexible material comprises equine pericardium that has been crosslinked and fixed in a low-concentration, buffered glutaraldehyde solution. Leaflets formed from this material are pliable and easy to open and close.

Equine pericardium that has been treated as discussed above can be supplied as a generally flat, thin and flexible sheet of material from which a plurality of leaflets can be cut. Other source materials, such as bovine pericardium and woven cloth, can also be obtained in flat sheets. Still further source materials may be obtained in irregular or curved shapes. For example, segments of intestinal tissue, some knitted cloths and some extruded polymers can be supplied having generally tubular geometry. Segments can be cut from such suitable source materials and then assembled to form the desired prosthesis. Various cutting media and methods, such as a razor, die cutter, laser or jet of fluid and/or particles can be used to cut segments from source material. In a preferred embodiment of the aortic heart valve discussed above, individual valve leaflets are cut from a sheet of treated equine pericardium.

Figure 5:
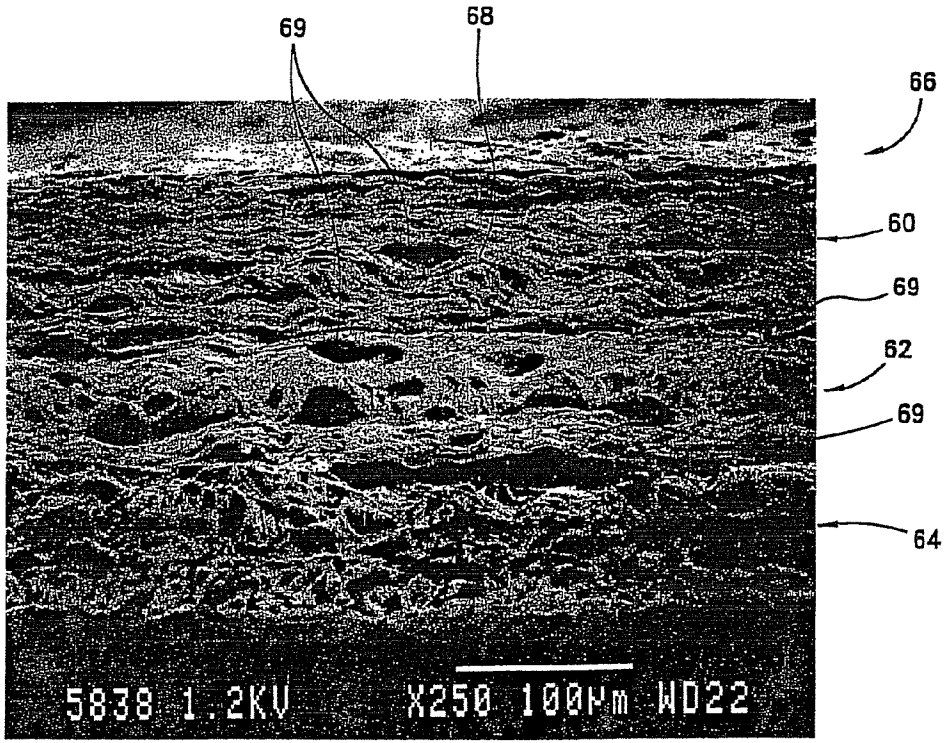
FIG. 5 is a scanning electron microscope image of an edge of an equine pericardium segment that has been cut with a razor.

With next reference to FIG. 5, equine pericardium has a laminar structure with three fibrous layers, the visceral 60, serosa 62, and parietal layers 64. Applicant has discovered that cutting equine pericardium using a contact-type cutter such as a razor or cutting die has a tendency to delaminate one or more of the layers along the cut edges. FIG. 5 is a scanning electron microscope image of an equine pericardium segment edge 66 that has been cut with a razor.

As can be seen in FIG. 5, each of the layers 60, 62, 64 has a generally different consistency. Additionally, the fibrous material 68 within each layer has several discontinuities and gaps 70. In this configuration, the cut edge 66 is especially susceptible to degradation due to external factors. For example, a fluid such as blood can fill some of the gaps 69 between the layers 60, 62, 64 or fibers 68 and can act as a wedge gradually disconnecting the layers or fibers from one another. Over time such delaminations would advance beyond just the cut edge, and may compromise the performance and strength of the prosthetic segment.

Delaminations of the fibrous layers of a heart valve leaflet can disrupt valve operation and significantly impair valve durability. For example, blood that enters between delaminated layers can cause a cuspal hemotoma or lead to calcification of the valve due to increased turbulence. Additionally, the strength of the leaflet can be reduced. Accordingly, it is desirable to reduce or eliminate delamination of the pericardium layers when constructing valves.

Other flexible materials used for heart valves, especially pericardial tissues, may have similar laminar structure, and may be subject to similar issues with regard to delamination. Challenges also arise when cutting synthetic materials such as woven or knit polymers, because the cut filaments or yarns may have a tendency to fray. Such fraying can cause problems similar to delamination.

Figure 6:
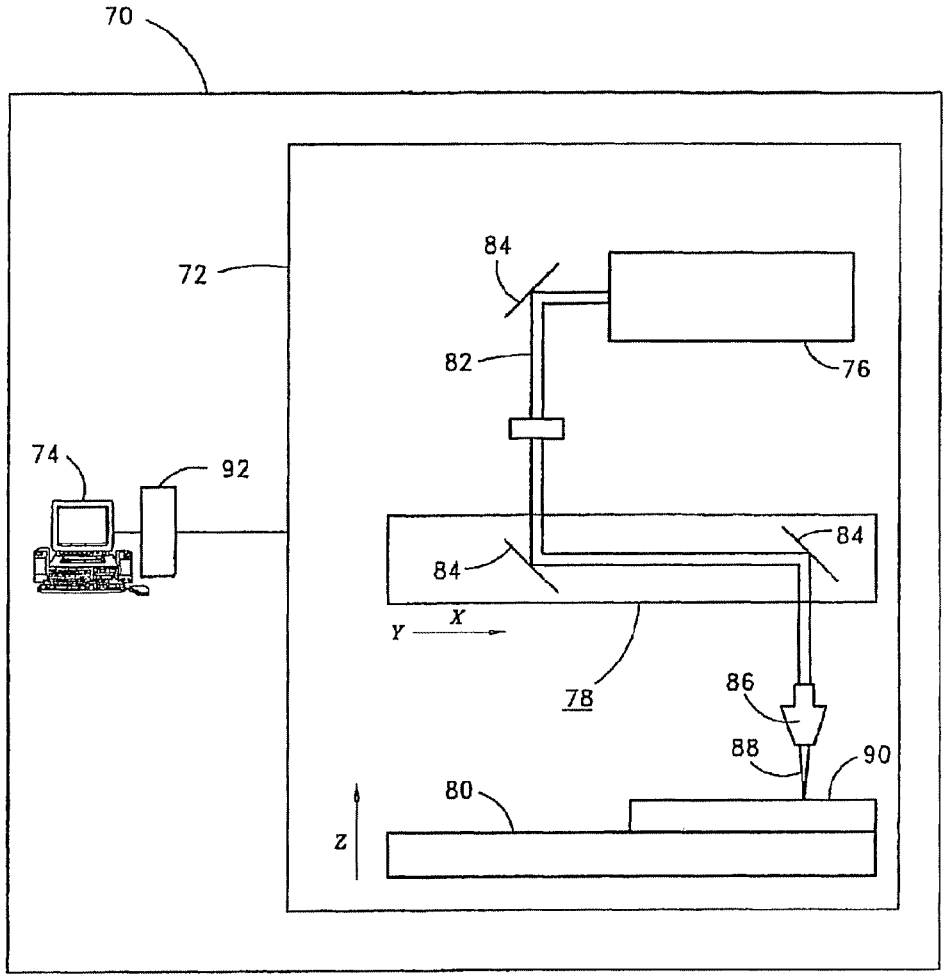
FIG. 6 is a schematic view of a plotted laser cutting apparatus for precision cutting of segments for implantable medical devices.

In accordance with one embodiment, a laser cutting apparatus 70 is provided for cutting prosthetic segments from source material 90. With reference specifically to FIG. 6, the laser cutting apparatus 70 comprises a laser system 72 and a computer 74. The laser system 72 comprises a laser tube assembly 76, a motion system 78 and a support platform 80. The laser tube assembly 76 is configured to create a laser beam 82 which is directed through a series of optic elements such as mirrors 84 and lenses 86 in order to direct a focused laser beam 88 on the support platform 80, which is configured to support the source material 90. The focused laser beam 88 is configured to cut through the source material 90 in order to cut out a segment according to a prescribed pattern.

The motion system 78 preferably is arranged to selectively locate and move the position of the focused laser beam 88 relative to the platform 80 in order to cut the segment out of the source material 90. In the illustrated embodiment, the motion system 78 can move the laser beam's position along horizontal X and Y axes. The support platform 80 is vertically movable along a vertical Z axis. It is to be understood that, in other embodiments, other types of motion systems can be employed.

Figure 7:
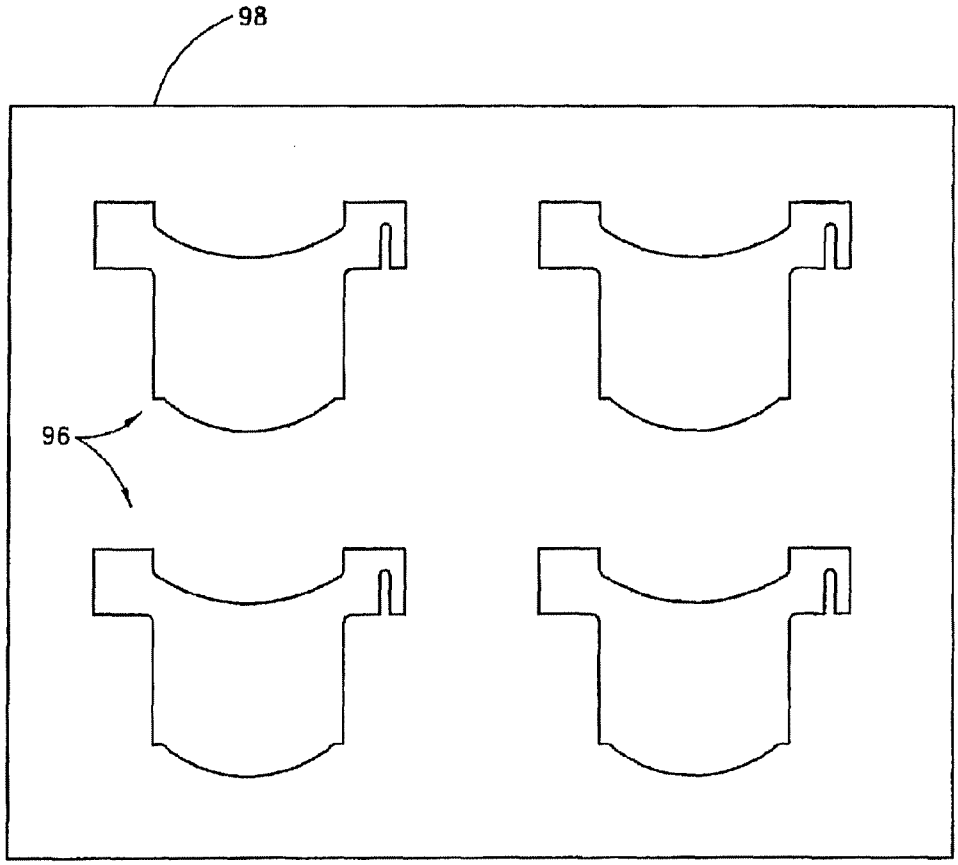
FIG. 7 is a plan view showing several aortic valve leaflets arranged to be cut by the plotted laser apparatus of FIG. 6.

The computer 74 preferably controls the laser system 72 via a printer driver 92, which communicates data from the computer 74 to the laser system 72 in order to control laser parameters and motion. In the illustrated embodiment, a computer assisted design (CAD) software program, such as Corel Draw®, is hosted by the computer 74. The CAD software is used to create designs of segments that will be cut. FIG. 7 shows a cutting pattern or template 96 created by CAD software. The template 96 functions as a target for the laser. The illustrated template 96 is configured so that four valve leaflets will be cut from a sheet 98 of source material.

In a preferred embodiment, the CAD software also functions as a command interface for submitting cutting patterns 96 to the laser system 72 through the printer driver 92. When directed to do so by the computer 74 and printer driver 92, the laser system 72 precisely cuts the patterns 96 from the source material 90.

The laser cutting apparatus 70 is configured to have a pulse power, cutting speed, and number of pulses per inch that will impart sufficient energy to vaporize portions of the source material along a cut line in order to cut the desired segment shape, and to at least partially melt the cut edges. Melting the cut edges effectively fuses or welds the layers and fibrous matter together.

Figure 8:
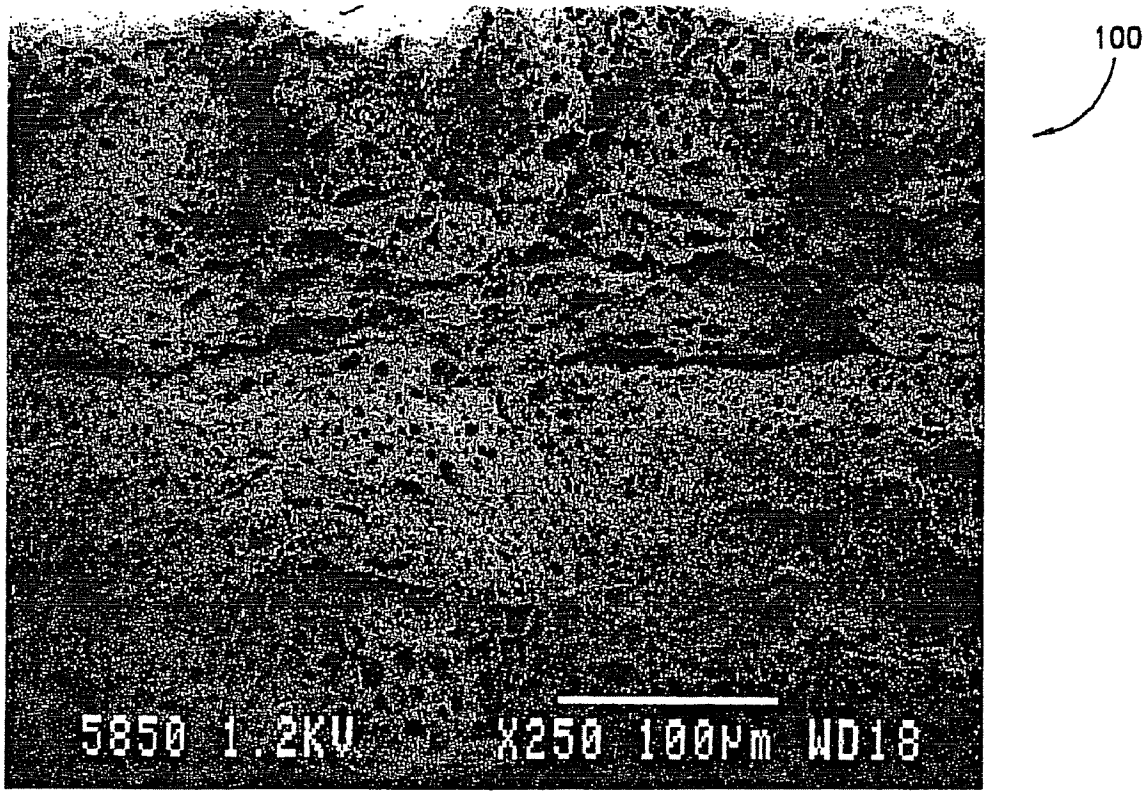
FIG. 8 is a scanning electron microscope image of an edge of a segment of equine pericardium that has been cut with the plotted laser cutting apparatus of FIG. 6.

Welding of the edges is especially advantageous for laminar materials such as pericardium, because the melted edge resists delamination. FIG. 8 is a scanning electron microscope image taken along a cut edge 100 of a sample of equine pericardial tissue that has been cut using a laser. When compared with FIG. 5, FIG. 8 shows that the characteristics of the laser-cut edge 100 are much different than the a razor-cut edge 66. As shown in FIG. 8, the visceral, serosa and parietal layers are no longer distinguishable when the material has been laser cut. Additionally, the generally fibrous, layered character of the pericardium has been changed along the cut edge 100. Applicant has found that heart valve leaflets with melted edges exhibit dramatically increased durability over leaflets that have been cut using more traditional die-cutting or razor-cutting methods.

An issue that arises during laser cutting is management of thermal energy. Excessive thermal energy absorbed by a source material such as pericardium can burn the material. Burning of the material can result in several types of damage. For example, the burned material can become stiff and brittle or can become biased to bend in a particular direction. Further characteristics of burning include discoloration or even charring of the material.

Burned portions of a segment of material can jeopardize the integrity and durability of the entire segment, and of a prosthesis constructed using that segment. For example, a stiffened or biased portion of a prosthetic heart valve leaflet will not move in the same manner as the rest of the leaflet during opening and closure of the valve. The hemodynamic performance of the valve thus could be compromised. Further, damage caused by burning of the material generally weakens the material and could reduce the durability of the valve. As such, it is desirable to weld the material at the cut edge, but avoid communicating thermal energy into the cut segment beyond the edge.

Excessive burning of the laser cut edge can also have a negative impact. If excessive laser energy is applied to the cut edge, it is more likely that thermal energy will be conducted beyond the edge and into the segment, resulting in tissue necrosis. Additionally, the tissue at an excessively-burned edge may have a somewhat inconsistent thickness, having portions that are significantly thicker than other portions or developing beads of melted material. Discoloration of the cut edge can indicate application of excessive thermal energy. Inconsistencies in the edge make the segment more difficult to work with during manufacture and can affect performance of the segment. As such, it is desirable to weld the material at the cut edge in a manner so that the melted edge is relatively uniform in thickness and consistency and exhibits minimal, if any, beading.

In a preferred embodiment, a $CO_2$ laser is used to laser cut heart valve leaflets out of a sheet of equine pericardial tissue about 0.35-0.55 mm thick. The laser system preferably is an M-series laser engraving and cutting system available from Universal Laser Systems, Inc. This device employs a 30 watt, pulsed, sealed $CO_2$ laser. The $CO_2$ laser produces laser light with a characteristic wavelength of 10.6 μm. Most non-metals, including equine pericardial tissue, are highly absorptive of laser energy at this wavelength, and also exhibit low thermal conductivity to such laser energy. Hence, the $CO_2$ laser is especially advantageous for cutting pericardial tissue because the tissue absorbs and is vaporized by the $CO_2$ laser light but very little or no thermal energy is conducted to regions of the tissue that are not being cut. Only the boundary/edge of the cut is melted, effectively forming a weld.

In the preferred embodiment, a sheet of equine pericardium is placed on the support surface 80. An operator directs the computer 74 to actuate the laser system 72, which cuts leaflets out of the sheet according to the prescribed pattern 96. To help maintain the tissue in good condition, it preferably is kept moist when being cut.

When cutting equine pericardium, the laser preferably is operated at a power of about 7.5 watts (joules/second). The laser can cut at a linear speed of about 1 inch per second, a pulse rate of about 1000 pulses per inch (PPI), and a laser spot diameter of about 0.003 inches.

A measurement of laser energy per pulse is computed by using the following equation (1):

$$[\text{laser energy per pulse (joules/pulse)}]=[\text{power (joules/second)}]/([\text{cutting speed (inches/second)}]\times[\text{pulse rate (pulses/inch)}]).$$

For the above embodiment, the laser energy per pulse is about:

$$(7.5\ \text{joules/second})/((1\ \text{inch/second})\times(1000\ \text{pulses/inch}))=0.0075\ \text{joules/pulse}.$$

Other materials, such as bovine or other kinds of pericardium tissues and laminar materials can also be advantageously laser cut with a $CO_2$ laser as discussed above. In another preferred embodiment wherein such materials, including equine pericardium, are laser cut, about 0.005-0.5 joules of laser energy are supplied per pulse, with a laser spot size of about 0.002 to 0.005 inches in diameter, a cutting speed of about 1 inch/second, and a pulse rate of about 1000 PPI. More preferably, about 0.005-0.02 joules of laser energy are supplied per pulse. For the Universal Laser Systems M-series laser discussed above, the following sample settings enable laser cutting within the above-discussed parameters: a 1.5 Lens, 20% power setting, 3.4% speed, 1000 PPI and 1000 dots per inch.

It is to be understood that if parameters such as the pulse rate and cutting speed are adjusted, corresponding adjustments to other parameters can be made so that the energy imparted to the material substantially stays within the desired parameters. In this manner, a generally uniform weld can be formed along a cut edge without discoloring the edge or imparting excessive heat to other portions of the segment.

It is also to be understood that other types of lasers, such as an erbium laser that generates a laser beam having a wavelength of about 2.7-3.0 μm, can suitably be used to cut segments. Such alternative lasers can be operated at settings so that the cut edges are welded as discussed above.

Alternative techniques may be employed for laser cutting of segments for use in prosthetics, such as disclosed in U.S. Patent Application Publication No. U.S. 2002/0091441, which was published on Jul. 11, 2002. The entire disclosure of this publication is hereby incorporated herein by reference.

Various types of tissue and man-made materials can be cut with a laser by using generally the same principles as discussed above. For example, other types of laminar tissue can be cut so that the cut edges are welded and have a generally uniform consistency with little or no discoloration. Similarly, for man-made materials such as woven or knitted polymers, the cut edges preferably are melted so that fraying of the woven filaments or yarns is minimized or avoided, but discoloration is also avoided.

Figure 9:
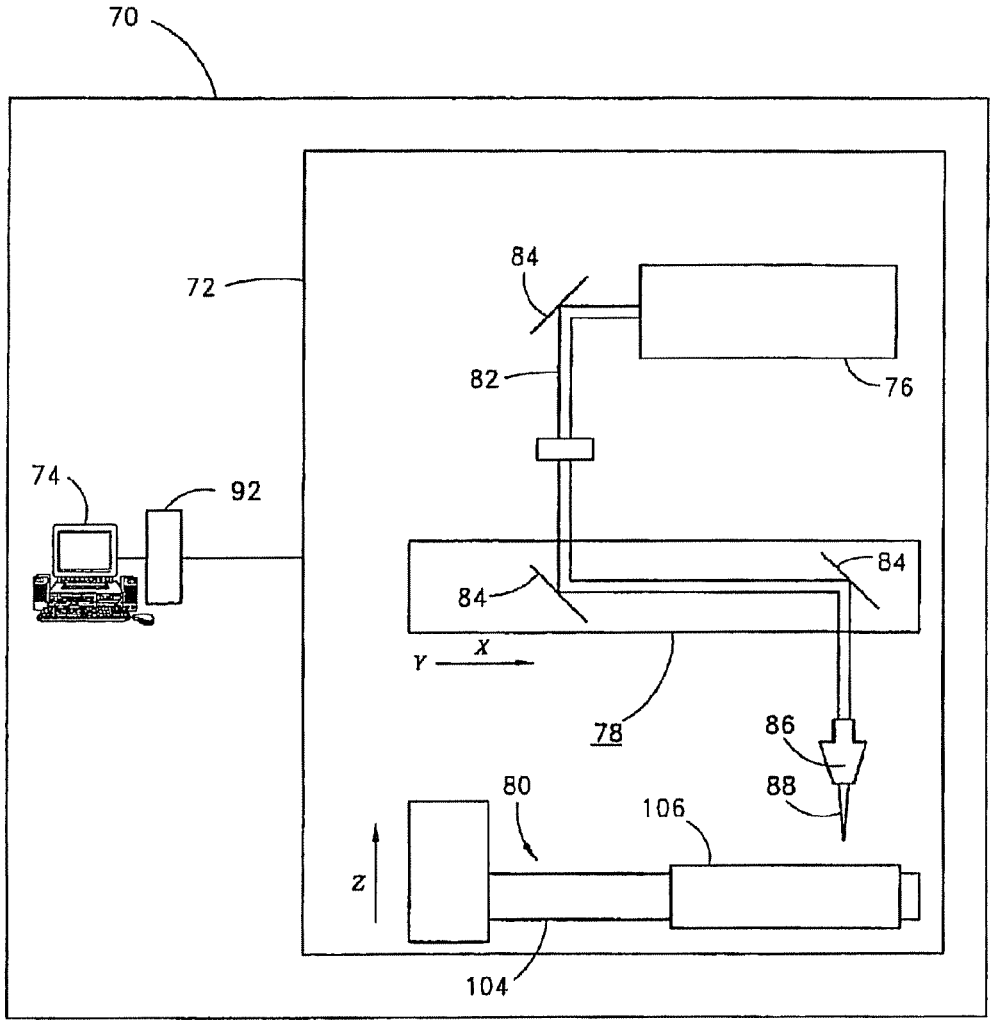
FIG. 9 is a schematic view of another embodiment of a plotted laser cutting apparatus for precision cutting of segments for implantable medical devices.

With reference next to FIG. 9, an embodiment of a laser cutting apparatus for cutting curved or tubular materials is illustrated. This embodiment is substantially similar to the embodiment presented in FIG. 6 except that the support surface 80 comprises a rotary axis 104 configured to accept a tubular source material 106. In addition to vertical movement about a Z-axis, the rotary axis 104 is adapted to rotate in order to help position the tubular source material 106 in an advantageous cutting position relative to the focused laser beam 88.

Although this invention has been disclosed in the context of certain preferred embodiments and examples, it will be understood by those skilled in the art that the present invention extends beyond the specifically disclosed embodiments to other alternative embodiments and/or uses of the invention and obvious modifications and equivalents thereof. In addition, while a number of variations of the invention have been shown and described in detail, other modifications, which are within the scope of this invention, will be readily apparent to those of skill in the art based upon this disclosure. It is also contemplated that various combinations or subcombinations of the specific features and aspects of the embodiments may be made and still fall within the scope of the invention. Accordingly, it should be understood that various features and aspects of the disclosed embodiments can be combined with or substituted for one another in order to form varying modes of the disclosed invention. Thus, it is intended that the scope of the present invention herein disclosed should not be limited by the particular disclosed embodiments described above, but should be determined only by a fair reading of the claims that follow.

What is claimed is:

1. A method of creating an implantable medical prosthesis, comprising:

providing a sheet of pericardium, wherein the pericardium has at least two tissue layers;

cutting a segment of tissue out of the sheet of pericardium with a laser beam;

said cutting comprising operating a laser at a power and pulse rate such that said beam welds the layers of the pericardium together along a laser cut edge;

wherein the laser is operated in a pulsed manner, supplying between about 0.005-0.5 joules of laser energy per pulse, with a laser spot size of about 0.002-0.005 inches in diameter, thereby producing a laser cut edge without significantly burning the pericardium adjacent the cut edge.

2. The method of claim 1, wherein the pericardium tissue comprises equine pericardium.

3. The method of claim 1, wherein the laser beam power and pulse rate are selected so that there is substantially no discoloration of the pericardium along the cut edge.

4. The method of claim 1, wherein the prosthesis comprises a heart valve, said cutting comprising cutting a plurality of segments of tissue out of the sheet of pericardium with the laser beam and attaching the cut segments to one another to form the valve.

5. The method of claim 1, comprising moving the laser beam at a cutting speed of about 1 inch per second and a pulse rate of about 1000 pulses per inch.

6. The method of claim 5, wherein the laser beam supplies between about 0.005-0.02 joules of laser energy per pulse.

7. The method of claim 1, wherein the laser beam operates at a wavelength of about 10.6 microns.

8. The method of claim 1, wherein the laser beam operates at a wavelength of about 2.7-3.0 microns.

9. The method of claim 1, wherein the laser energy is about 0.0075 joules per pulse and a laser spot diameter of about 0.003 inches.

* * * * *

UNITED STATES PATENT AND TRADEMARK OFFICE

CERTIFICATE OF CORRECTION

PATENT NO. : RE42,857 E
APPLICATION NO. : 12/765356
DATED : October 18, 2011
INVENTOR(S) : Cali et al.

It is certified that error appears in the above-identified patent and that said Letters Patent is hereby corrected as shown below:

On the Title Page:

Item [64], Replace sub-heading, PCT Filed: with sub-heading, Filed.

Signed and Sealed this
First Day of November, 2011

David J. Kappos

David J. Kappos
*Director of the United States Patent and Trademark Office*